United States Patent [19]
Liu et al.

[11] Patent Number: 6,068,991
[45] Date of Patent: May 30, 2000

[54] HIGH EXPRESSION *ESCHERICHIA COLI* EXPRESSION VECTOR

[75] Inventors: Suo W. Liu, Manlius; Thomas J. Franceschini, Cicero, both of N.Y.

[73] Assignee: Bristol-Myers Squibb Company, Princeton, N.J.

[21] Appl. No.: 09/205,428

[22] Filed: Dec. 4, 1998

Related U.S. Application Data

[60] Provisional application No. 60/069,751, Dec. 16, 1997.

[51] Int. Cl.[7] .............................. C12P 21/06; C12N 1/20; C12N 15/63; C12N 15/70
[52] U.S. Cl. .................. 435/69.1; 435/320.1; 435/252.3; 435/252.33; 435/71.3
[58] Field of Search ................................ 435/320.1, 69.1, 435/71.3, 252.3, 252.33

[56] References Cited

U.S. PATENT DOCUMENTS

| | | | |
|---|---|---|---|
| 4,342,832 | 8/1982 | Goeddel et al. | 435/91.41 |
| 4,366,246 | 12/1982 | Riggs | 435/69.8 |
| 4,425,437 | 1/1984 | Riggs | 435/320.1 |
| 4,431,739 | 2/1984 | Riggs | 435/252.33 |
| 4,551,433 | 11/1985 | DeBoer | 435/252.33 |
| 4,704,362 | 11/1987 | Itakura et al. | 435/252.3 |
| 5,053,335 | 10/1991 | Schumacher et al. | 435/230 |
| 5,221,619 | 6/1993 | Itakura et al. | 435/69.4 |
| 5,232,840 | 8/1993 | Olins | 435/69.1 |
| 5,635,391 | 6/1997 | Petre et al. | 435/252.3 |
| 5,776,724 | 7/1998 | Hartl et al. | 435/68.1 |

OTHER PUBLICATIONS

Castanié et al., Analytical Biochemistry 254(1):150–152 (1997).
Lee et al., J. Biol. Chem. 267(5):2849–2852 (1992).
Weiss et al., Proc. Natl. Acad. Sci. USA, vol. 81, pp 6019–6023, Oct. 1984.

*Primary Examiner*—Remy Yucel
*Attorney, Agent, or Firm*—Christopher A. Klein; Thomas R. Savitsky

[57] ABSTRACT

High expression vectors for expression of heterologous genes in *Escherichia coli*. The expression vectors contain, the tac promoter, an intergenic region, a restriction site, and, optionally, groES DNA.

24 Claims, 11 Drawing Sheets

SEQUENCE LISTING

<160> NUMBER OF SEQ ID NOS: 26

<210> SEQ ID NO 1
<211> LENGTH: 32
<212> TYPE: DNA
<213> ORGANISM: Escherichia coli

<400> SEQUENCE: 1
ctcaaaggag agttatccat ggatattcgt cc                32

<210> SEQ ID NO 2
<211> LENGTH: 32
<212> TYPE: DNA
<213> ORGANISM: Escherichia coli

<400> SEQUENCE: 2
cagacatttc tgcccggggg tttgtttatt tc                32

<210> SEQ ID NO 3
<211> LENGTH: 20
<212> TYPE: DNA
<213> ORGANISM: Escherichia coli

<400> SEQUENCE: 3
cagaggatat catgaaaaat                              20

<210> SEQ ID NO 4
<211> LENGTH: 26
<212> TYPE: DNA
<213> ORGANISM: Escherichia coli

```
<400> SEQUENCE: 4
accaggatcc aacatcacaa tacctg                                    26

<210> SEQ ID NO 5
<211> LENGTH: 12
<212> TYPE: DNA
<213> ORGANISM: Escherichia coli

<400> SEQUENCE: 5
gatctccatg gg                                                   12

<210> SEQ ID NO 6
<211> LENGTH: 12
<212> TYPE: DNA
<213> ORGANISM: Escherichia coli

<400> SEQUENCE: 6
gatccccatg ga                                                   12

<210> SEQ ID NO 7
<211> LENGTH: 52
<212> TYPE: DNA
<213> ORGANISM: Escherichia coli

<400> SEQUENCE: 7
aattgttgaa gcgtaatccg cgcacgacac tgaacatacg aatttaagga at       52

<210> SEQ ID NO 8
<211> LENGTH: 48
<212> TYPE: DNA
<213> ORGANISM: Escherichia coli

<400> SEQUENCE: 8
attccttaaa ttcgtatgtt cagtgtcgtg cgcggattac gcttcaac            48

<210> SEQ ID NO 9
<211> LENGTH: 6
<212> TYPE: DNA
<213> ORGANISM: Escherichia coli

<400> SEQUENCE: 9 aaagat                                                          6

<210> SEQ ID NO 10
<211> LENGTH: 10
<212> TYPE: DNA
<213> ORGANISM: Escherichia coli

<400> SEQUENCE: 10
catgatcttt                                                      10

<210> SEQ ID NO 11
<211> LENGTH: 64
<212> TYPE: DNA
<213> ORGANISM: Escherichia coli

<400> SEQUENCE: 11
aattgttgaa gcgtaatccg cgcacgacac tgaacataat ttaaggaata aagatcatca    60
cccg                                                            64

<210> SEQ ID NO 12
```

-continued

```
<211> LENGTH: 63
<212> TYPE: DNA
<213> ORGANISM: Escherichia coli

<400> SEQUENCE: 12
gatcgggtga tcatctttat tccttaaatt atgttcagtg tcgtgcgcgg attacgcttc      60
aac                                                                   63

<210> SEQ ID NO 13
<211> LENGTH: 64
<212> TYPE: DNA
<213> ORGANISM: Escherichia coli

<400> SEQUENCE: 13
aattgttgaa gcgtaatccg cgcacgacac tgaacataat ttaaggaata aagaccatgg      60
cccg                                                                  64

<210> SEQ ID NO 14
<211> LENGTH: 63
<212> TYPE: DNA
<213> ORGANISM: Escherichia coli

<400> SEQUENCE: 14
gatcgggcca tggtctttat tccttaaatt atgttcagtg tcgtgcgcgg attacgcttc      60
aac                                                                   63

<210> SEQ ID NO 15
<211> LENGTH: 62
<212> TYPE: DNA
<213> ORGANISM: Escherichia coli

<400> SEQUENCE: 15
aattgttgaa gcgtaatccg cgcacgacac tgaacataat ttaaggaata aacatatgcc      60
cg                                                                    62

<210> SEQ ID NO 16
<211> LENGTH: 60
<212> TYPE: DNA
<213> ORGANISM: Escherichia coli

<400> SEQUENCE: 16
gatcggcata tgtttattcc ttaaattatg ttcagtgtcg tgcgcggatt acgcttcaac      60

<210> SEQ ID NO 17
<211> LENGTH: 70
<212> TYPE: DNA
<213> ORGANISM: Escherichia coli

<400> SEQUENCE: 17
agcttgttga caattaatca acggctcgta taatgtgtgg aattgtgagc ggataacaat      60
ttccgcgcac                                                            70

<210> SEQ ID NO 18
<211> LENGTH: 66
<212> TYPE: DNA
<213> ORGANISM: Escherichia coli

<400> SEQUENCE: 18
acaactgtta attagttgcc gagcatatta cacccttaa cactcgccta ttcttaaagg       60
cgcgag                                                                66
```

<210> SEQ ID NO 19
<211> LENGTH: 70
<212> TYPE: DNA
<213> ORGANISM: Escherichia coli

<400> SEQUENCE: 19
gacactgaac atacgaattt aaggaataaa gatctgtgac ttgtatgctt aaattcctta    60
tttctagtac                                                          70

<210> SEQ ID NO 20
<211> LENGTH: 70
<212> TYPE: DNA
<213> ORGANISM: Escherichia coli

<400> SEQUENCE: 20
agcttgttga caattaatca acggctcgta taatgtgtgg aattgtgagc ggataacaat    60
ttaaggaaga                                                          70

<210> SEQ ID NO 21
<211> LENGTH: 66
<212> TYPE: DNA
<213> ORGANISM: Escherichia coli

<400> SEQUENCE: 21
acaactgtta attagttgcc gagcatatta cacaccttaa cactcgccta ttcttaaatt    60
cctat                                                               66

<210> SEQ ID NO 22
<211> LENGTH: 14
<212> TYPE: DNA
<213> ORGANISM: Escherichia coli

<400> SEQUENCE: 22
aagatttcta gtac                                                     14

<210> SEQ ID NO 23
<211> LENGTH: 68
<212> TYPE: DNA
<213> ORGANISM: Escherichia coli

<400> SEQUENCE: 23
agcttactcc ccatccccct gttgacaatt aatcatcggc tcgtataatg tgtggtccgc    60
gcacgaca                                                            68

<210> SEQ ID NO 24
<211> LENGTH: 64
<212> TYPE: DNA
<213> ORGANISM: Escherichia coli

<400> SEQUENCE: 24
tgtcgtgcgc ggaccacaca ttatacgagc cgatgattaa ttgtcaacag ggggatgggg    60
agta                                                                64

<210> SEQ ID NO 25
<211> LENGTH: 31
<212> TYPE: DNA
<213> ORGANISM: Escherichia coli

<400> SEQUENCE: 25

```
              -continued ctgaacatac gaatttaagg aataaaaaga c                          31

<210> SEQ ID NO 26
<211> LENGTH: 35
<212> TYPE: DNA
<213> ORGANISM: Escherichia coli

<400> SEQUENCE: 26
catggtcttt ttattcctta aattcgtatg ttcag                      35
```

HIGH EXPRESSION ESCHERICHIA COLI EXPRESSION VECTOR

This application claims the benefit of provisional application Ser. No. 60/069,751, filed Dec. 16, 1997, now abandoned.

FIELD OF THE INVENTION

The present invention concerns high expression vectors for expression of heterologous genes in bacteria such as *Escherichia coli*.

BACKGROUND OF THE INVENTION

The ability to express large quantities of recombinant proteins is desirable in many applications and of economical necessity for many industries. This is especially true for products that are of low value, products with small profit margin, technical enzymes (e.g., protease and lipases for detergents) and proteins for in vivo diagnostics (cholesterol oxidase, penicillin-G acylase). There are several expression systems available for the expression of heterologous genes. However, the most valuable, versatile and perhaps the best system for the expression of heterologous proteins is *Escherichia coli*. There are many publications on the essential elements needed to express heterologous proteins in high levels. One of the most essential elements is the promoter used to express the heterologous genes. The promoter used should be strong. Some of the more frequently used strong promoters for the expression of heterologous genes are the promoters from $P_L$, tac, trp, trc and the T7 promoter described by Studier et al. The promoters used are generally regulatable. This feature is essential if the target protein to be expressed is toxic to the host. In general, the stronger the promoter, the more RNA will be transcribed from the DNA leading to the accumulation of messenger RNA. Besides strong regulatable promoters, other elements are also involved in the expression of heterologous genes. The efficiency of the translation is involved in maximizing the expression of heterologous genes. The efficiency of translation can be affected by the mRNA 5'-terminus sequences as well as by the 5' end hairpin structure of the mRNA. Generally, a functional ribosome binding site containing a Shine-Dalgarno (SD) sequence properly positioned to an AUG initiation codon is essential for efficient translation. Variation in the distance between the SD sequence and the AUG codon are known to affect mRNA translation. Studies have also shown when the SD sequence or the AUG initiation codon is sequestered in a double-stranded region of the mRNA, translation is less efficient due to the blocking of the accessibility of these sequences to the ribosome. Some other factors that have been reported to affect the efficient expression of heterologous genes are the stability of the messenger RNAs, the susceptibilities of the protein products to proteolysis and the effect of the host genetic background. Although there is a wealth of information about the elements that affect the overall efficiency of a plasmid based expression system, there are other elements that have not been studied which may be involved in the expression of heterologous genes.

SUMMARY OF THE INVENTION

The present invention is directed to an expression vector comprising:
(a) tac promoter,
(b) groESL intergenic region of DNA,
(c) the start codon of the groEL gene sequence, and
(d) a restriction site.
In a preferred embodiment the expression vector of the invention further comprises: (e) groES DNA.

In another aspect the present invention concerns a prokaryotic host cell containing an expression vector comprising:
(a) tac promoter,
(b) groESL intergenic region of DNA,
(c) the start codon of the groEL gene sequence,
(d) a restriction site, and, optionally,
(e) groES DNA In another aspect the present invention is also directed to a method for producing a heterologous protein comprising culturing a host cell of the invention under conditions suitable for expression of the protein.

DETAILED DESCRIPTION OF THE INVENTION

Figure 1A:
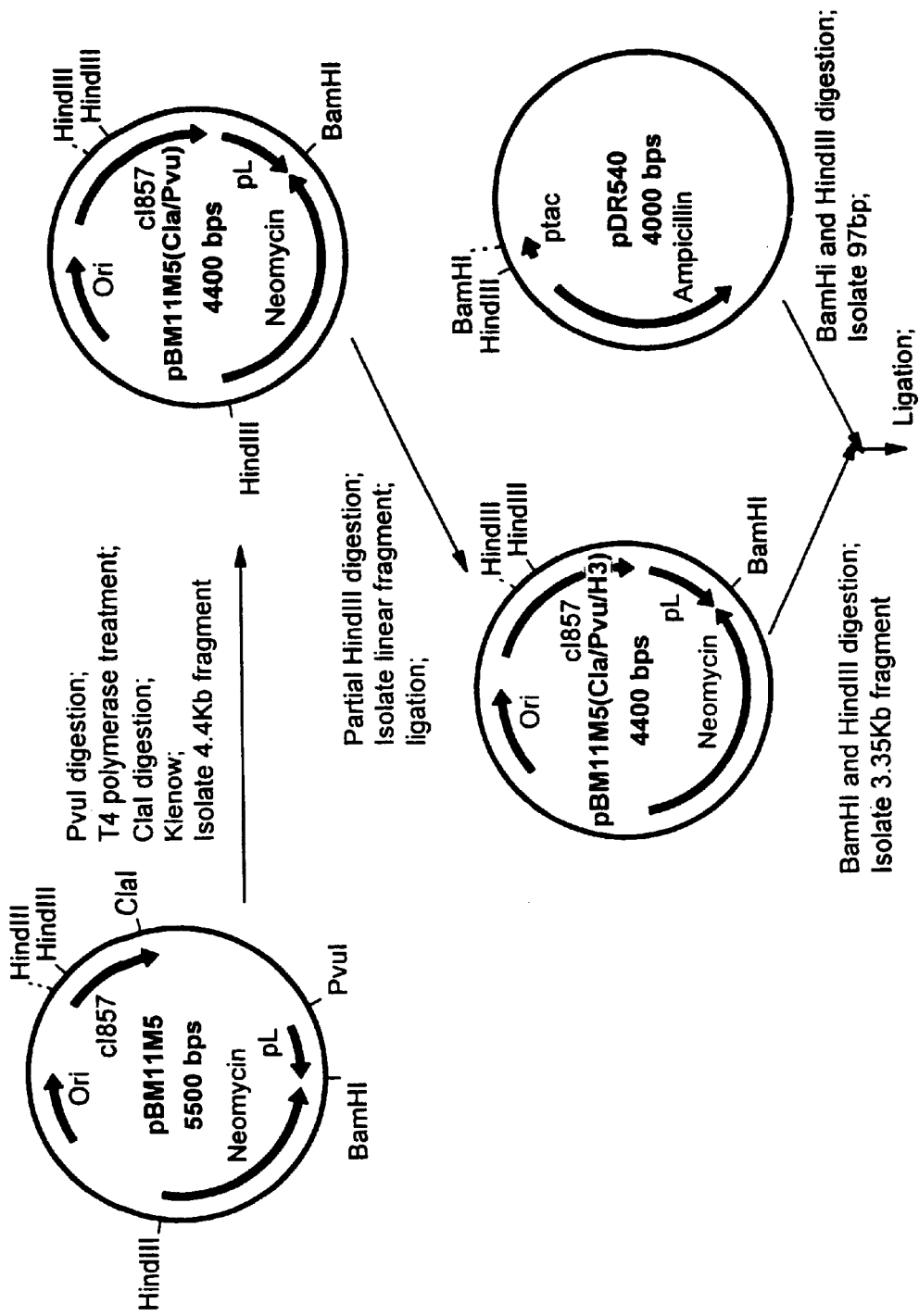
FIG. 1. Construction of pBMS1000.
Figure 1B:
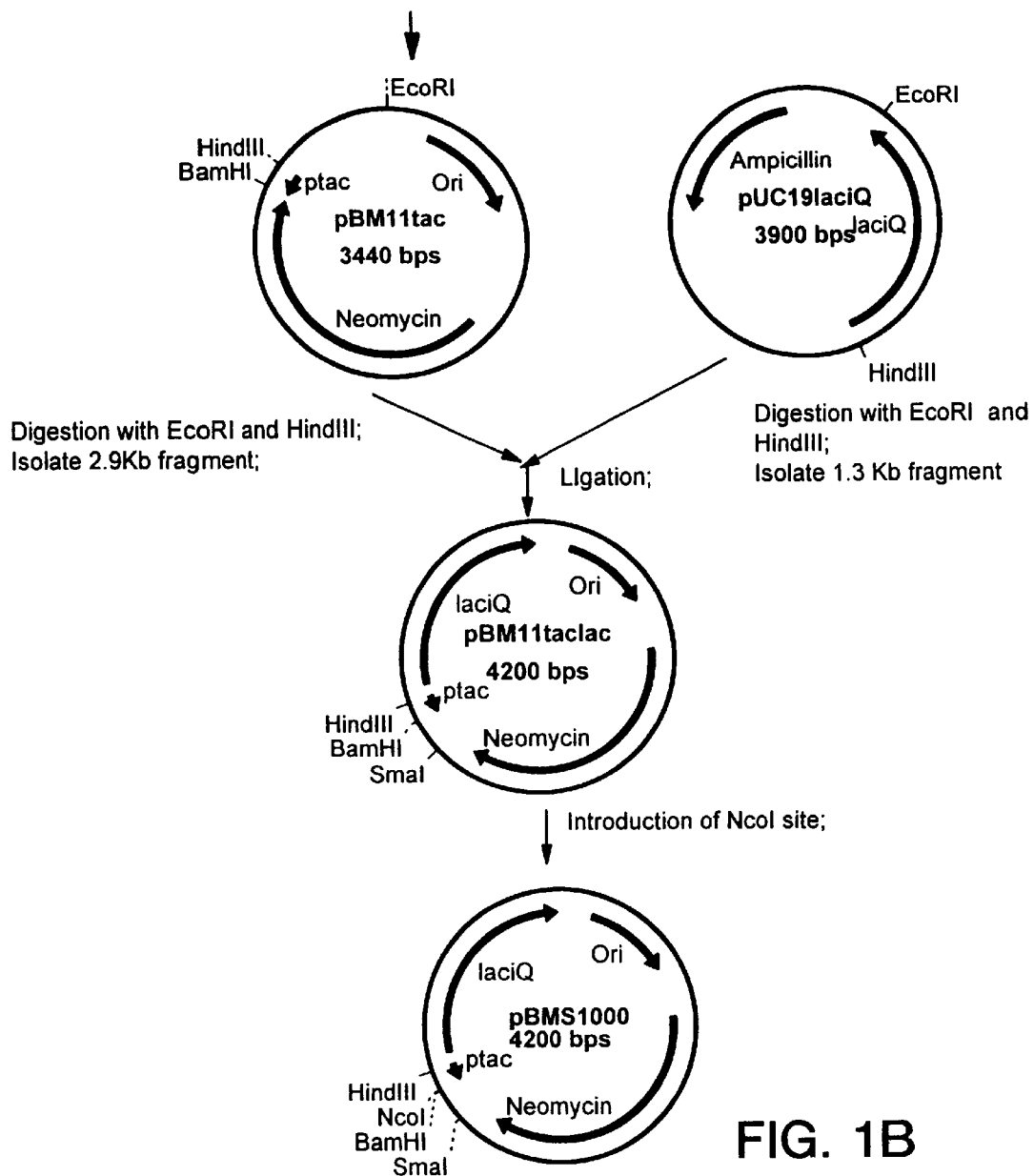
Figure 2:
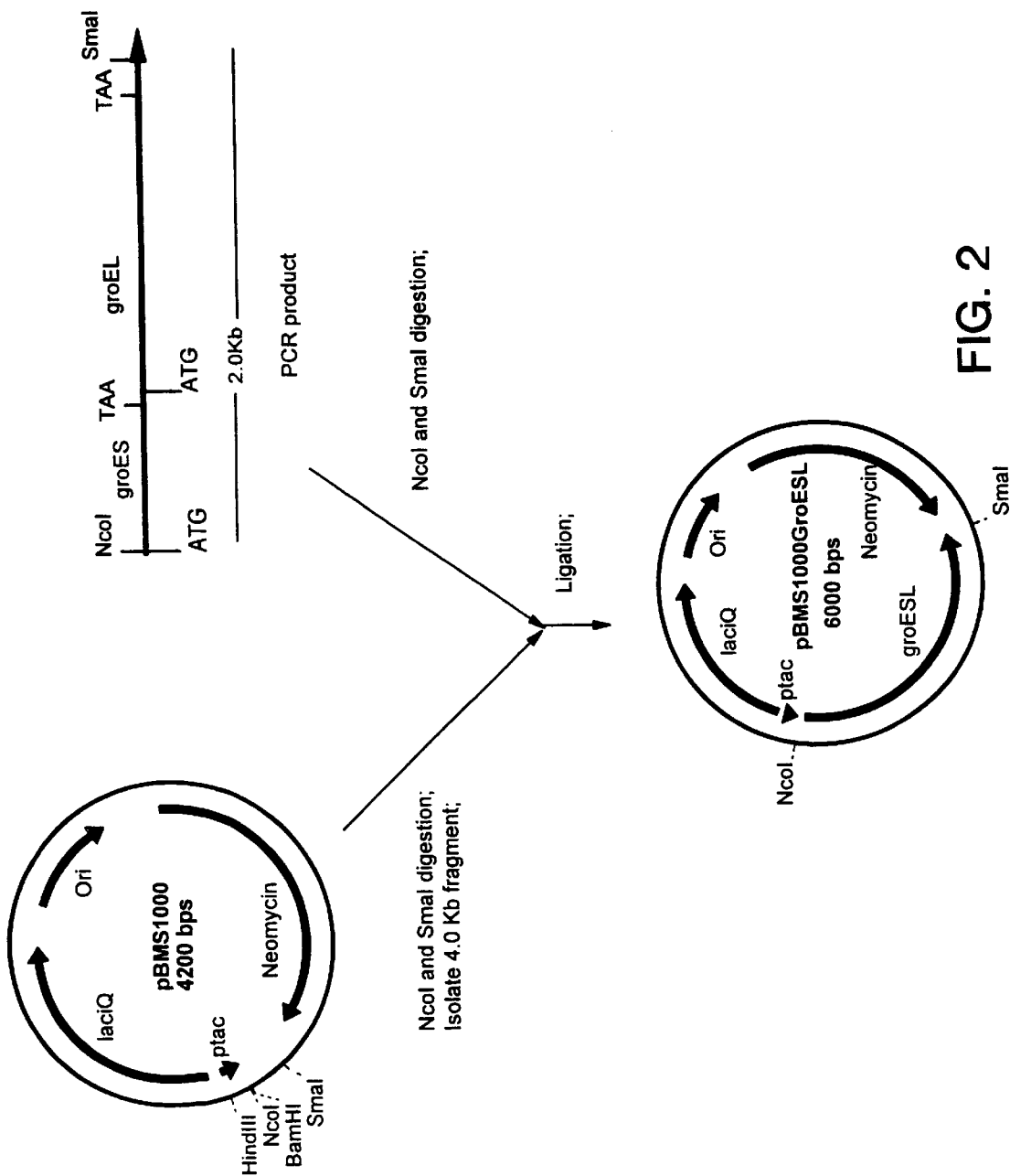
FIG. 2. Construction of pBMS1000GroESL.
Figure 3:
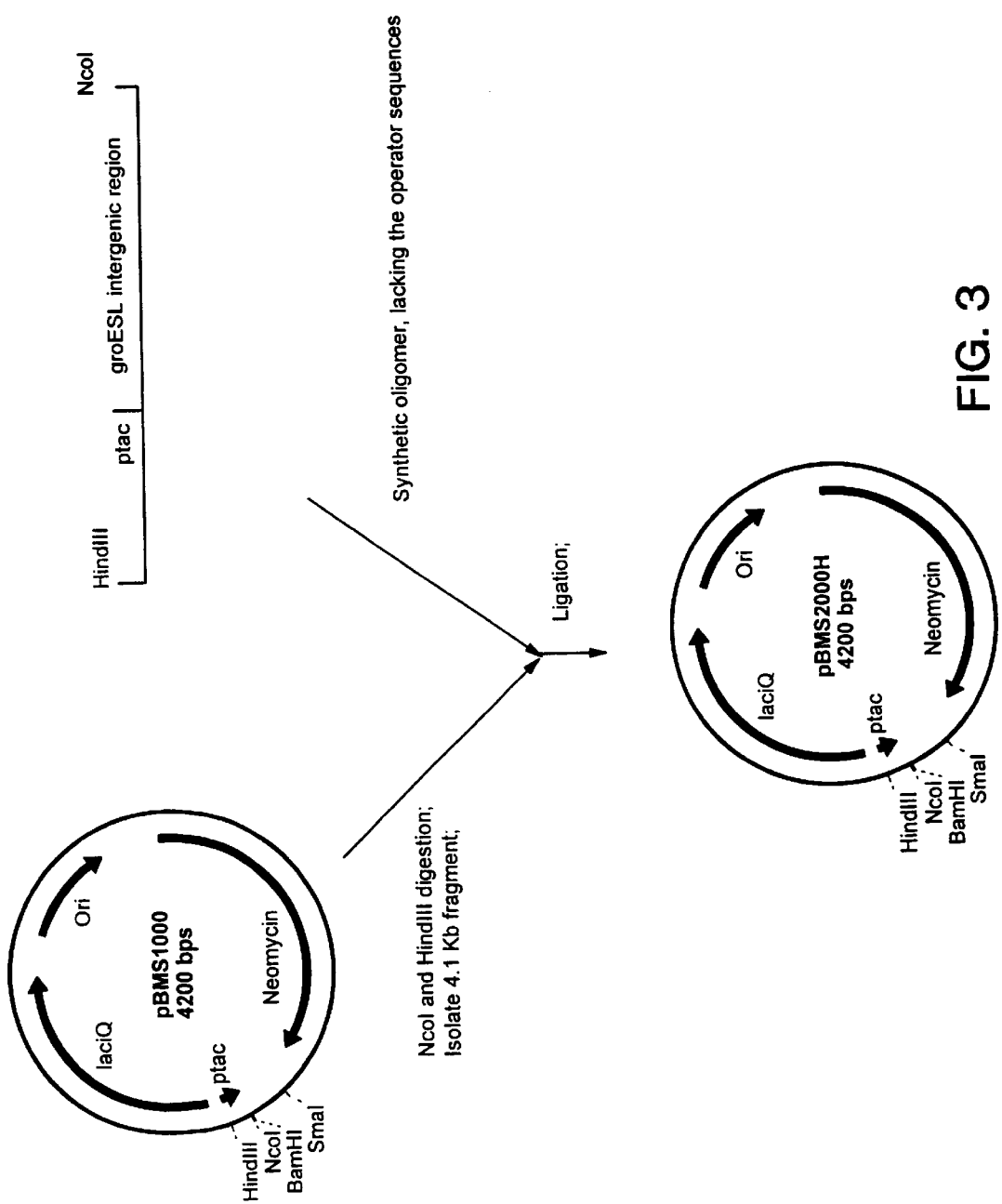
FIG. 3. Construction of pBMS2000H.
Figure 4:
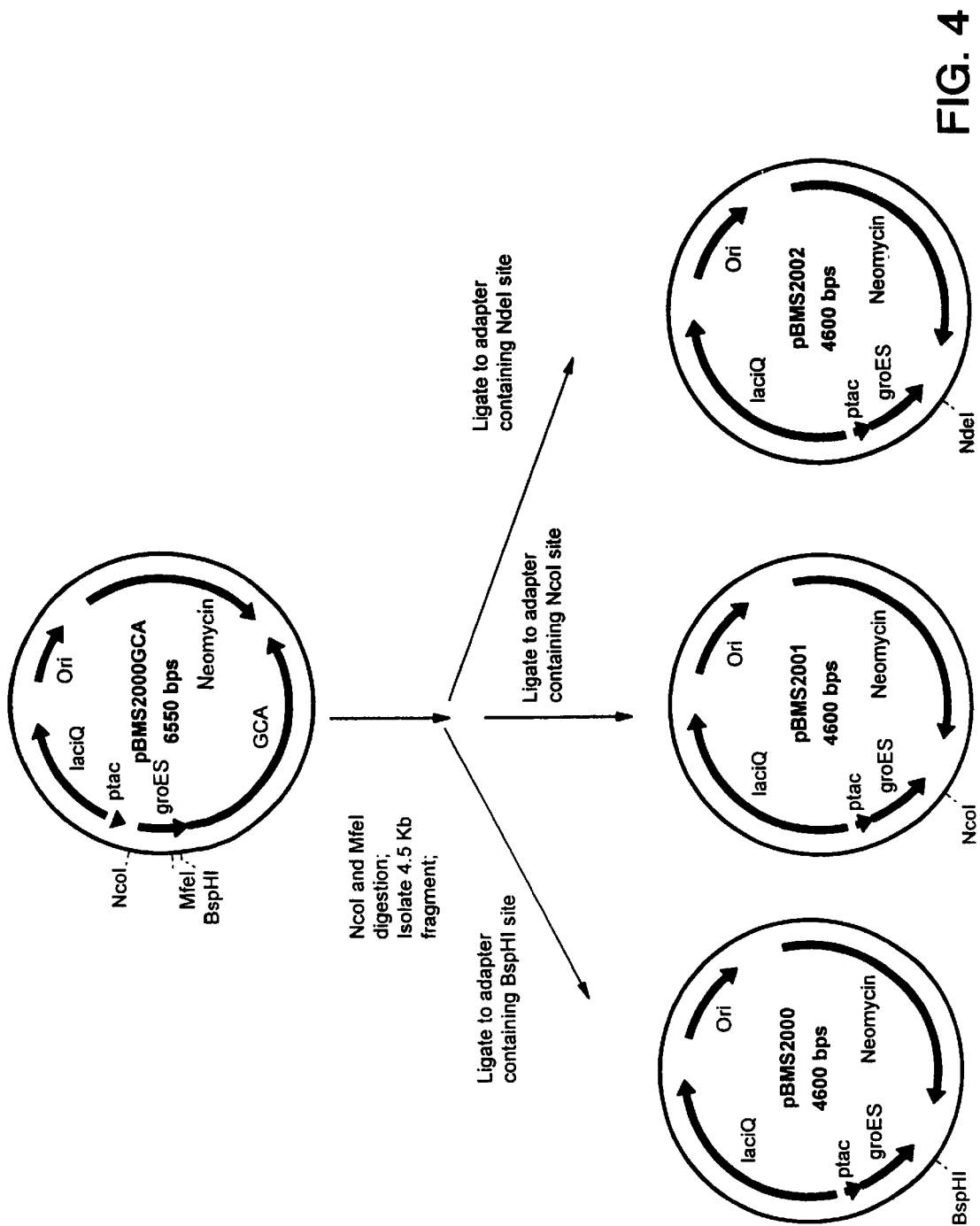
FIG. 4. Construction of pBMS2000, pBMS2001, pBMS2002.
Figure 5:
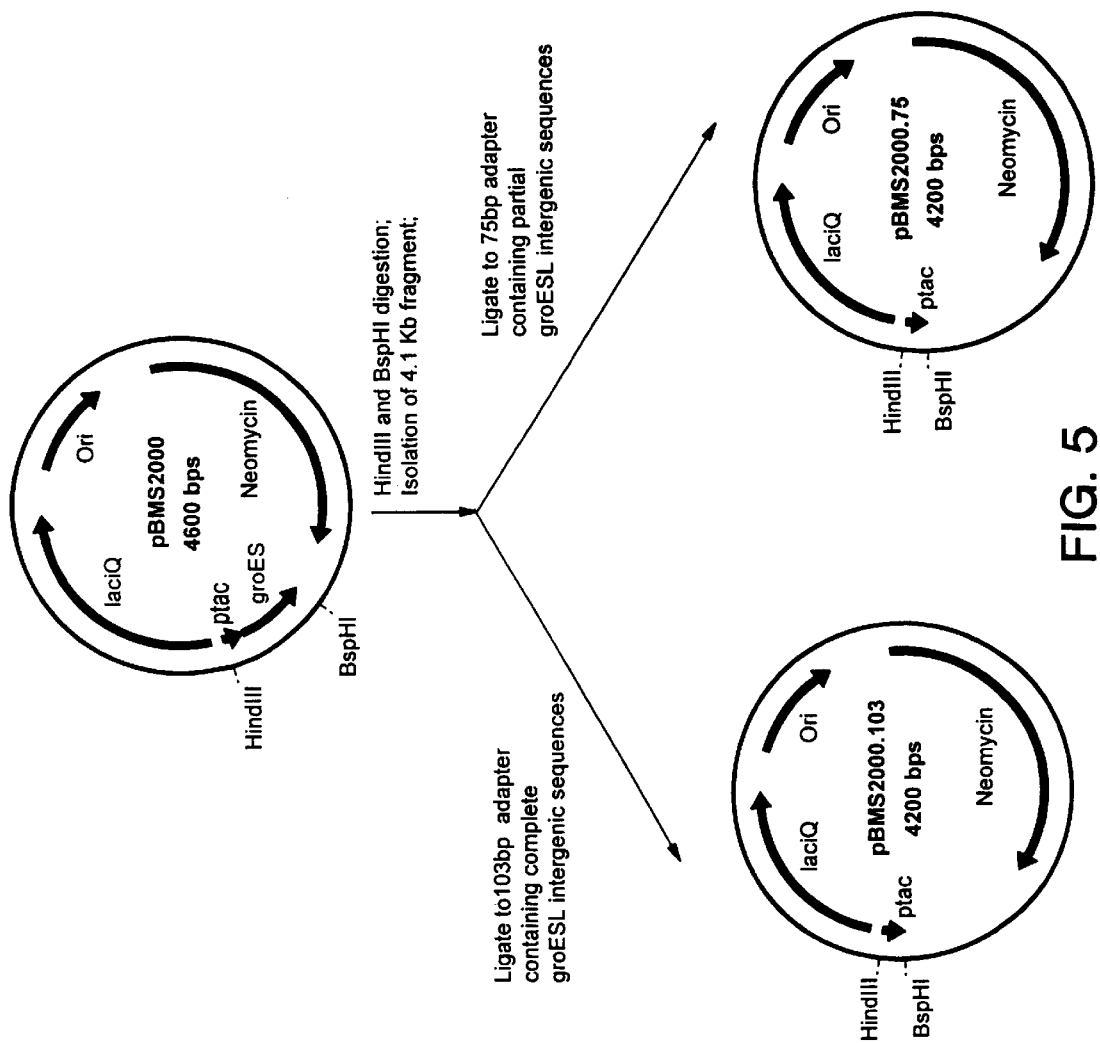
FIG. 5. Construction of pBMS2000.103 and pBMS2000.75.
Figure 6:
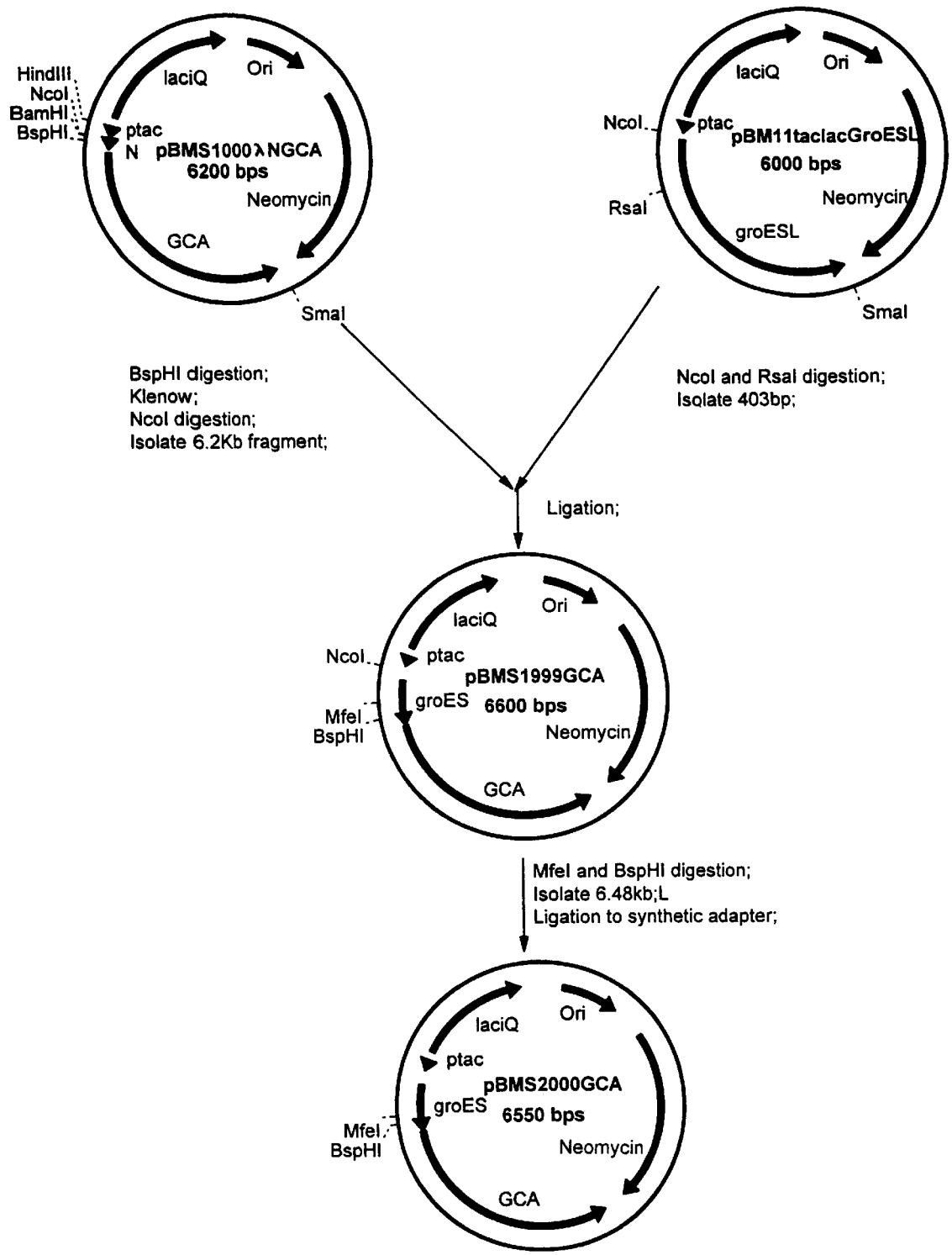
FIG. 6. Construction of pBMS1999GCA and pBMS2000GCA.
Figure 7A:
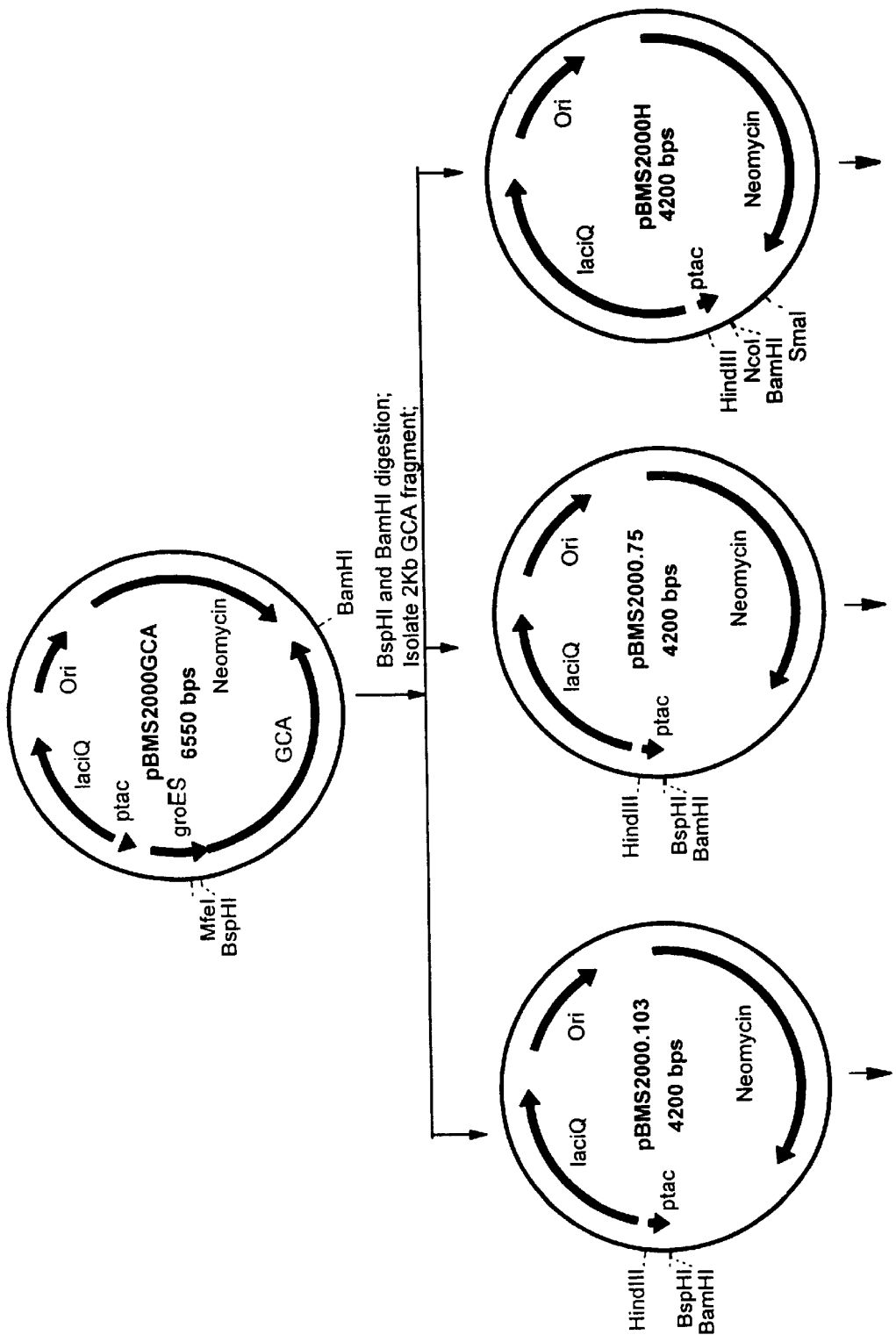
FIG. 7. Construction of pBMS2000.103GCA, pBMS2000.75GCA, and pBMS2000HGCA.
Figure 7B:
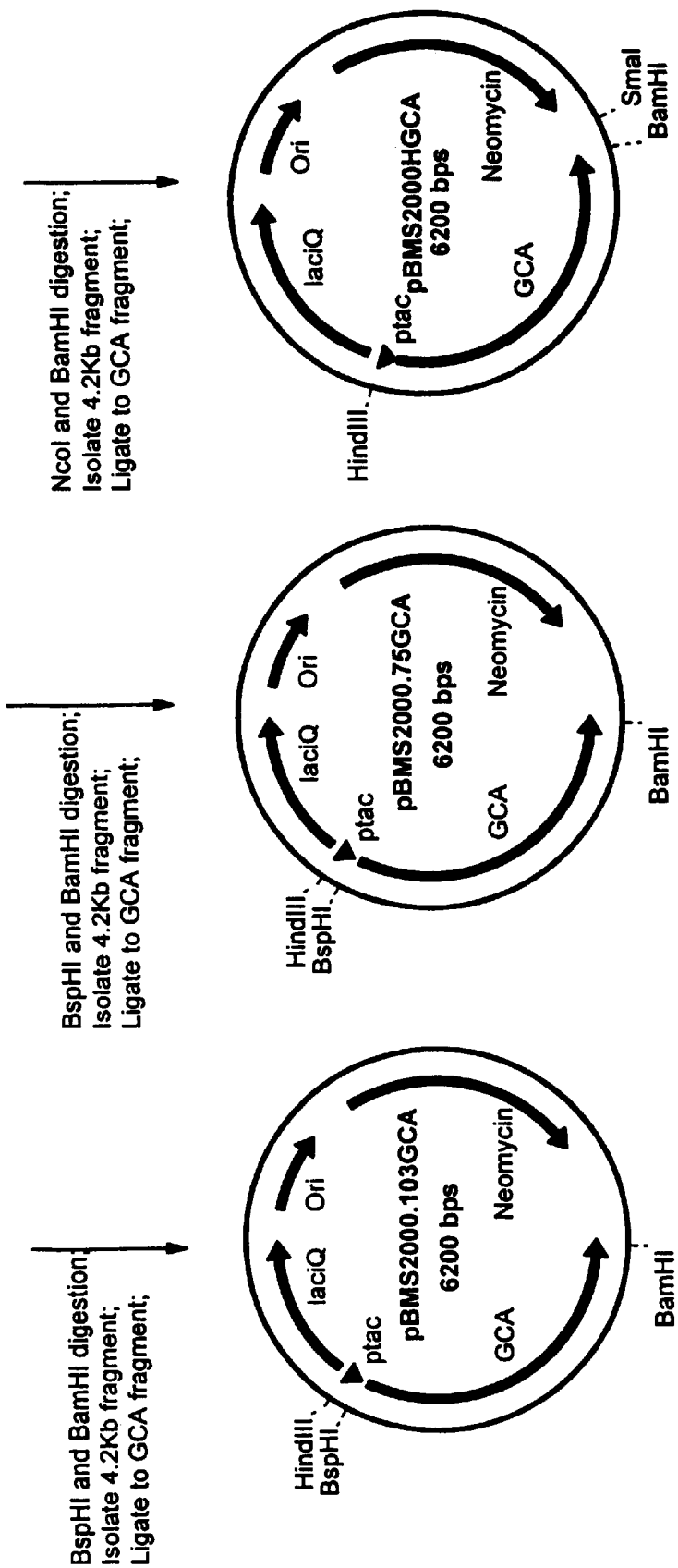
Figure 8A:
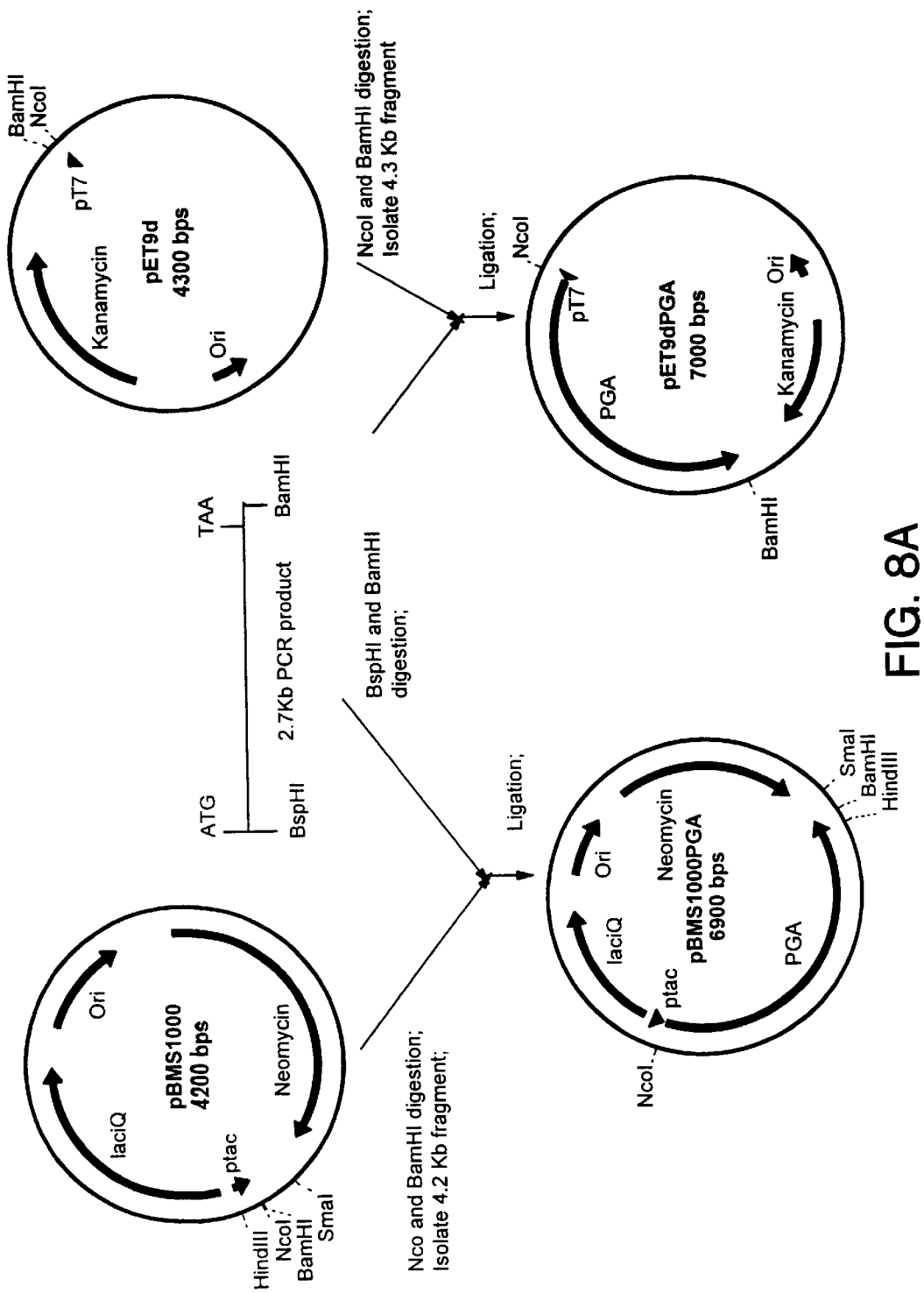
FIG. 8. Construction of pBMS1000PGA, pET9dPGA, and pBMS2000PGA.
Figure 8B:
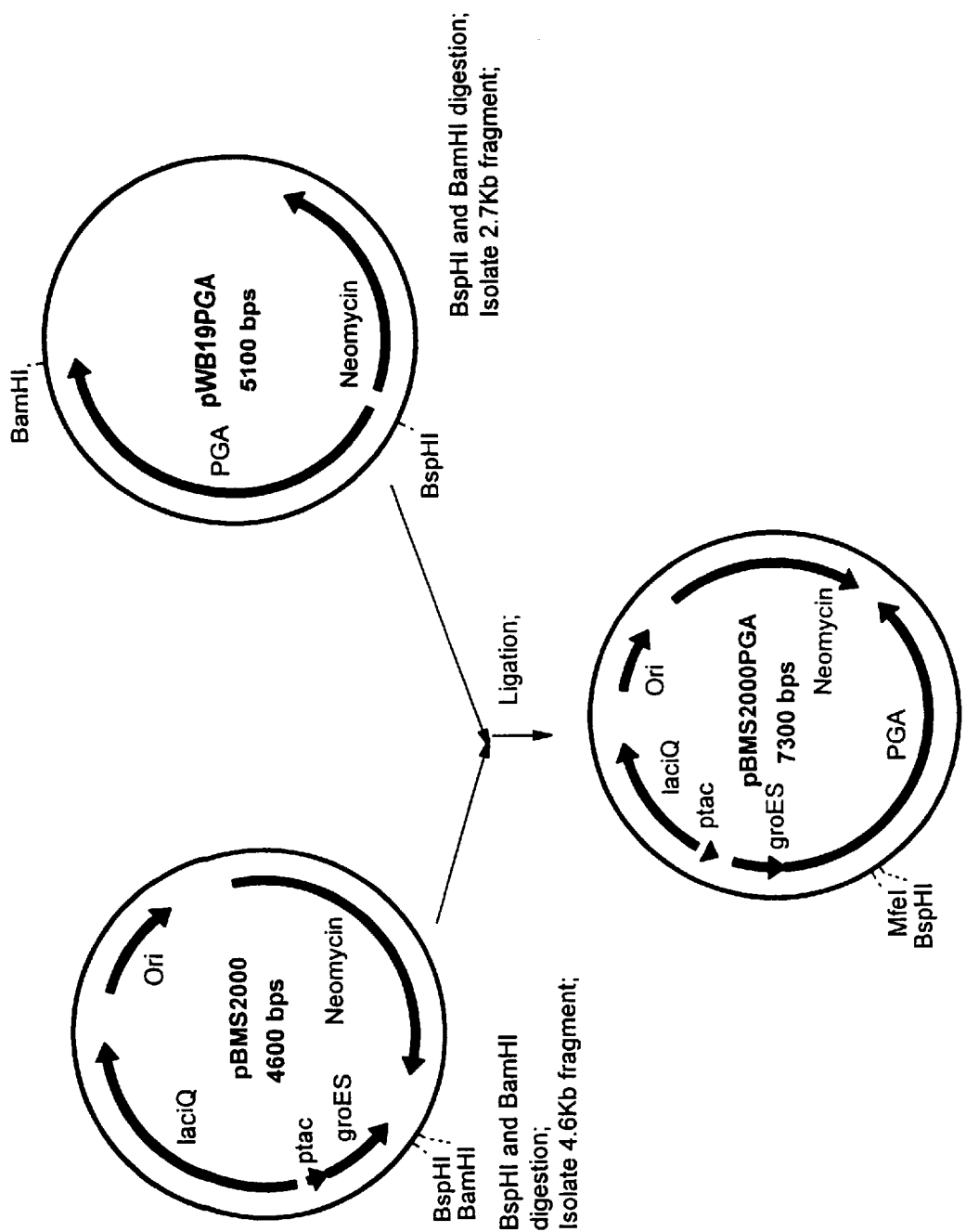

The *Escherichia coli* GroES and GroEL are chaperone proteins which mediate the correct folding of a wide variety of polypeptides and facilitate oligomeric protein assembly by preventing premature interior intramolecular interactions that can lead to aggregation or misfolding structure. The GroES and the GroEL proteins are transcribed from the same mRNA. The expression vectors of the invention are based on the GroESL operon.

Expression vectors of utility in the present invention are often in the form of "plasmids", which refer to circular double stranded DNA loops which, in their vector form, are not bound to the chromosome. However, the invention is intended to include such other forms of expression vectors which serve equivalent functions and which become known in the art subsequently hereto.

The vectors of the invention are capable of expressing heterologous genes in large quantities in *Escherichia coli*. In addition to other features, the vectors of the invention preferably have an origin of replication and a nucleic acid sequence coding for a selectable marker. The particular selectable marker used is not critical provided the marker allows for phenotypic selection in transformed host cells. Preferred selectable markers are antibiotic resistance. Examples of antibiotic resistance markers include ampicillin, tetracycline, chloramphenicol, kanamycin, gentamycin, nalidixic acid, rifampicin, spectinomycin, streptomycin, neomycin phosphotransferase, and the like.

In the vectors of the invention, the tac promoter is followed by (i.e., upstream of) the complete gene sequence of the groES gene, which is followed by the intergenic region between the termination codon of the groES gene which is followed by the start codon of the groEL gene (termed herein the "groESL intergenic region"), which is followed by a restriction cloning site. The restriction cloning site can be introduced immediately at the start codon of the groEL gene or at the RsaI site in the coding region of the the groEL gene. Heterologous gene cloned into the former expression vectors will be expressed as the native protein whereas heterologous gene cloned into the latter expression vectors will be expressed as a fusion protein to the first 7 amino acids of the groEL gene. The cloning restriction sites supply the codon, ATG, the codon needed for the initiation of the translation.

The vectors of the invention can be categorized into two classes, those containing the groES gene and those without the groES gene. The first class of vectors contain the strong regulatable promoter, tac, followed by the codons coding for the gene GroES. In the vectors of the invention a cloning site is introduced into the RsaI site of the gene coding for GroEL or a cloning site is introduced immediately before the start codon of the GroEL gene. As stated above,in the former case, the gene product will be a fusion protein containing approximately 7 amino acids of the GroEL gene at the amino terminus; in the latter case, the gene product will be the native protein containing the amino acid methionine at the amino terminus. In both types of constructs, all the GroEL sequences after the introduced restriction site preferably are removed. In the second type of vectors, the vectors contain the tac promoter followed by various length of the intergenic sequences between the groES and groEL gene and a restriction site which supply the initiation codon for the cloning of heterologous genes. The groES gene has been eliminated.

The deletion of the groES gene sequences can be advantageous in some cases. The co-expression of the groES protein in large quantities may interfere with downstream processing, such as the immobilizaton of the enzymes to solid supports. However, in other instances it may be advantageous to use an expression vector containing the gene sequences for the groES gene (e.g., pBMS2000) because it can stabilize the transcripts and the presence of groES may stabilize the heterlogous protein expressed.

The vectors of the invention also optionally contain sequences coding for the lac repressor to regulate the transcription from the lac promoter; this allows expression of the heterologous gene cloned to be controlled by isopropyl-β-D-thiogalactopyranoside (IPTG) or lactose.

In a variation of the above mentioned expression vectors, vectors contemplated herein optionally express heterologous genes constitutively. This is accomplished by removing the operator sequences from the promoter region. An example of such a vector is plasmid pBMS2000H. Advantages in using a constitutive expression vector include elimination of the need to add an inducer to induce the system to express the heterologous gene products. This can decrease the cost of goods and simplify fermentation process by eliminating one fermentation parameter needed to be examined such as the optimal IPTG concentration and the optimal time to add the inducer to yield optimal expression of the gene product. It is possible, in some cases, that the cloning of heterologous genes in constitutive expression vectors will yield more heterologous gene products as the gene products are accumulated from the very beginning of the cell growth.

The regulatory DNA sequences of the vectors of the invention, such as the promoter and repressor, are operatively linked to the DNA sequence coding for all or part of the heterologous gene sequence desired to be expressed. As used in this context, the term "operatively linked" means that the regulatory DNA sequences are capable of directing the replication and/or the expression of the DNA sequence coding for all or part of the protein desired to be expressed.

The vectors of the invention can be used to express a wide variety of heterologous genes. Examples of heterologous genes that can be expressed using the vectors of the invention include D-amino acid oxidase gene from *Trignopsis variabilis*; genes encoding immunotoxins such as G28.5sFv-PE40 and BR110sFv-PE40; the gene coding for penicillin G amidase, the gene coding for the glutaryl cephalosporin amidase (GCA), and the like. As shown in the Examples section, the vectors of the invention yield higher titers of expressed enzymes (e.g., GCA), relative to other vectors known in the art, such as T-7 RNA polymerase based pET vectors.

The expression vectors of the invention may also include other DNA sequences known in the art, for example, stability leader sequences which provide for stability of the expression product, secretory leader sequences which provide for secretion of the expression product, stability elements which provide mitotic stability to the plasmid, and other sequences which provide additional sites for cleavage by restriction endonucleases. The characteristics of the actual expression vector used must be compatible with the host cell which is to be employed.

The sequence for the tac promoter is described in, for example, Weiss et al. Proc. Natl. Acad. Sci. U.S.A. 81, p. 6019–6023, 1984.

Suitable expression vectors containing the desired coding and control sequences may be constructed using standard recombinant DNA techniques as taught herein or as known in the art, many of which are described in T. Maniatis et al., Molecular Cloning: A Laboratory Manual, Cold Spring Harbor Laboratory, Cold Spring Harbor, N.Y., 1982.

The present invention additionally concerns host cells containing an expression vector of the invention. Suitable host cells are prokaryotic cells which are preferably biologically pure. Suitable prokaryotic host cells include, for example, *Escherichia coli*, *Bacillus subtilus* and *Salmonella typhimurum* cells. The most preferred host cell of the invention is *E. coli* DH5α mcr which is also designated ATCC 98563. *E. coli* ATCC 98563 was deposited with the American Type Culture Collection, 10801 University Boulevard, Manassas, Va. 20110-2209 on Oct. 28, 1997, under the provisions of the Budapest Treaty. *E. coli* ATCC 98563 contains plasmid pBMS2000.

Expression vectors may be introduced into host cells by various methods known in the art. For example, transfection of host cells with expression vectors can be carried out by the calcium phosphate precipitation method. However, other methods for introducing expression vectors into host cells, for example, electroporation, biolistic fusion, liposomal fusion, nuclear injection, viral or phage infection or protoplast fusion, can also be employed.

Once an expression vector has been introduced into an appropriate host cell, the host cell may be cultured under conditions permitting expression of the desired protein or polypeptide.

Host cells containing an expression vector of the invention may be identified by one or more of the following six general approaches: (a) DNA-DNA hybridization; (b) the presence or absence of marker gene functions; (c) assessing the level of transcription as measured by the production of hTOPI mRNA transcripts in the host cells; (d) detection of the gene product immunologically; (e) complementation analysis; and (f) enzyme assay, enzyme assay being the preferred method of identification.

In the first approach, the presence of a DNA sequence coding for the desired heterologous protein can be detected by DNA-DNA or RNA-DNA hybridization using probes complementary to the DNA sequence.

In the second approach, the recombinant expression vector host system can be identified and selected based upon the presence or absence of certain marker gene functions (e.g., thymidine kinase activity, resistance to antibiotics, uracil prototrophy, etc.). A marker gene can be placed in the same plasmid as the DNA sequence coding for the heterologous gene under the regulation of the same or a different promoter used to regulate heterologous protein production. Expression of the marker gene in response to induction or selection indicates expression of the DNA sequence coding for the heterologous protein.

In the third approach, the production of heterologous gene mRNA transcripts can be assessed by hybridization assays. For example, RNA can be isolated and analyzed by Northern blotting or nuclease protection assay using a probe complementary to the RNA sequence. Alternatively, the total nucleic acids of the host cell may be extracted and assayed or hybridization to such probes.

In the fourth approach, the expression of the heterologous gene can be assessed immunologically, for example, by Western blotting.

In the fifth approach, the expression of the heterologous gene can be assessed by complementation analysis. For example, in cells known to be deficient in an enzyme of interest, expression of enzyme activity can be inferred by improved growth of cells under growth-limiting conditions.

In the sixth approach, expression of heterologous DNA can be measured by assaying for enzyme activity using known methods. For example, the assay described in Y. Pommier, J. Biol. Chem., 265, pages 9418–9422, 1990 may be employed.

The DNA sequences of expression vectors, plasmids or DNA molecules of the present invention may be determined by various methods known in the art. For example, the dideoxy chain termination method as described in Sanger et al., Proc. Natl. Acad. Sci. USA, 74, pages 5463–5467, 1977, or the Maxam-Gilbert method as described in Proc. Natl. Acad. Sci. USA, 74, pages 560–564, 1977 may be employed.

It should, for course, be understood that not all expression vectors and DNA regulatory sequences will function equally well to express the DNA sequences of the present invention. Neither will all host cells function equally well with the same expression system. However, one of ordinary skill in the art may make a selection among expression vectors, DNA regulatory sequences, and host cells using the guidance provided herein without undue experimentation and without departing from the scope of the present invention.

The present invention is also directed to a method for producing a heterologous protein comprising culturing a host cell of the invention under conditions suitable for expression of the protein.

Growth of the host cells may be achieved by one of ordinary skill in the art by the use of an appropriate medium. Appropriate media for growing host cells include those which provide nutrients necessary for the growth of the cells. A typical medium for growth includes necessary carbon sources, nitrogen sources, and trace elements. Inducers may also be added. The term "inducer", as used herein, includes any compound enhancing formation of the desired protein or peptide. Carbon sources may include sugars such as glucose, sucrose, lactose, galactose, raffinose, and the like; nitrogen sources include yeast extract, casamino acids, N-Z amine, bacto-tryptone, and the like. A preferred medium comprises 2.4% yeast extract, 1.2% Bacto-tryptone, 0.4% glycerol, 0.72M dipotassium hydrogen phosphate and 0.17M potassium dihydrogen phosphate. The pH of the medium is preferably adjusted to about 6.8 to 7.5, more preferably about 7.0.

The process of the present invention is performed under conditions suitable for expression of the desired peptide. The pH of the medium is preferably maintained between about 7.0 and 7.5, most preferably between about 7.0 and 7.2, during the growth of host cells. A suitable temperature range for the process of the invention is from about 25° C. to about 37° C. Pressure is not known to be critical to practice of the invention and for convenience about atmospheric pressure is typically employed. The process of the invention is preferably carried out under aerobic conditions.

The following example is to illustrate the invention but should not be interpreted as a limitation thereon.

EXAMPLE
MICROBIAL STRAINS AND PLASMIDS

The plasmids and *Escherichia coli* strains are listed in Table 1

TABLE 1

| Strain and Plasmids | Relevant Characteristics |
|---|---|
| BL21 | F$^-$ompT hsdS$_B$(r$_B^-$m$_B^-$) gal dcm |
| BL21(DE3) | F$^-$ompT hsdS$_B$(r$_B^-$m$_B^-$) gal dcm (λDE3) |
| DH5αMCR | F$^-$mcrAΔ(mrr-hsdRMS-mcrBC)f80lacZΔM15(lacZYA-argF U169endA1recA1deoRthi-1 supE44I-gyrA96relA1 |
| UM262 | recA KatG::Tn10 pro leu rspL hsdR endl lacY |
| W3110(ATCC 27325) | λ$^-$,F$^-$, prototrophic |
| pBM11M5 | Canadian patent #1335357 |
| pBMS1000 | Neo$^R$, 4.2 Kb |
| pBMS1000GroESL | Neo$^R$, 6.2 Kb |
| pBMS2000 | Neo$^R$, 4.6 Kb |
| pBMS2001 | Neo$^R$, 4.6 Kb |
| pBMS2002 | Neo$^R$, 4.6 Kb |
| pBMS2000.75 | Neo$^R$, 4.2 Kb |
| pBMS2000.103 | Neo$^R$, 4.2 Kb |
| pBMS2000H | Neo$^R$, 4.2 Kb |
| pBMS1000GCA | Neo$^R$, 6.15 Kb |
| pBMS1999GCA | Neo$^R$, 6.6 Kb |
| pBMS2000GCA | Neo$^R$, 6.55 Kb |
| pBMS2000.103GCA | Neo$^R$, 6.2 Kb |
| pBMS2000.75GCA | Neo$^R$, 6.2 Kb |
| pBMS2000HGCA | Neo$^R$, 6.2 Kb |
| pBMS1000PGA | Neo$^R$, 6.9 Kb |
| pBMS2000PGA | Neo$^R$, 7.3 Kb |
| pET9dPGA | Neo$^R$, 7.0 Kb |

Buffer and Media

Lauria Broth: 1% Difco Bacto tryptone, 0.5% Difco Bacto yeast extract, 0.5% sodium chloride Lauria agar: Lauria broth supplemented with 1.5% Difco Bacto agar T broth: 1.2% Difco Bacto tryptone, 2.4% Difco Bacto yeast extract, 0.72M dipotassium hydrogen phosphate, 0.17M potassium dihydrogen phosphate, 0.4% glycerol PCR Amplification of Promoterless groES and groEL Genes The forward and the reverse PCR primers were synthesized with ABI 391 DNA Synthesizer. The forward primer (5'CTCAAAGGAGAGTTATCCATGGATATTCGTCC3') (SEQ.ID.NO.:1)was designed to introduce a NcoI restriction site at the start codon of the groES gene. The reverse primer (5'CAGACATTTCTGCCCGGGGGTTTGTTTATTTC3') (SEQ.ID.NO.:2)was designed to be approximately 23 bases from the groEL translation termination codon which included a natural SmaI site. The DNA from *Escherichia coli* XG44 was amplified in a 50 μl reaction containing standard PCR buffer. The reactions were performed on the GeneAmp® PCR System 2400 DNA Thermal Cycler (Perkin-Elmer) DNA Thermal Cycle using 0.25 ml microtubes. The PCR conditions consisted of the initial denaturing step at 95° C. for 4 minutes followed by 32 cycles of denaturation at 95° C. for 45 seconds, primer annealing at 58° C. for 1 minute, and primer extension at 72° C. for 3 minutes. Upon final extension of the cycling steps, a final extension at 72° C. for 20 minutes was performed before the reaction was stored at 4° C. The resultant PCR products were digested with restriction enzymes NcoI and SmaI and separated on a 0.7% agarose gel. The desired 2.0 Kb DNA fragment was excised from the gel, electroeluted and precipitated with ethanol. The purified DNA was used for subsequent cloning.

PCR Amplification of Penicillin G Amidase Gene

The penicillin G amidase gene was amplified from *E. coli* XG44 genomic DNA by PCR using specific forward primer (CAGAGGATA<u>TCATGA</u>AAAAT) (SEQ.ID.NO.:3)which introduces an BspHI restriction site and reverse primer (ACCA<u>GGATCC</u>AACATCACAATACCTG) (SEQ.ID.NO.:4) which introduces a BamH I restriction site. The PCR condition consisted of the initial denaturing step at 95° C. for 2 minutes followed by 33 cycles of denaturation at 94° C. for 1 minute, primer annealing at 55° C. for 1 minute, and primer extension at 72° C. for 2 minutes. Upon final extension of the cycling steps, a final extension at 72° C. for 5 minutes was performed before the reaction was stored at 4° C.

Induction of Bacterial Cultures for the Expression of Heterologous Genes

The cells harboring the recombinant genes were grown overnight in T-broth in the presence of 30μg/ml of neomycin sulfate. The next day, the cultures were diluted 1:10 with T-broth supplemented with appropriate antibiotic. The cells were grown at 30° C. in a gyratory incubator for 4hours and/or to the optical density of 2.0 at 600 nm at which time appropriate concentration of isopropyl-β-D-thiogalactopyranoside (IPTG) was added to the culture. The cultures were continued incubated in the presence of IPTG at 30° C. for an additional four hours.

Assay of Glutaryl Cephalosporin Amidase

The detection of glutaryl cephalosporin amidase (GCA) was based on the conversion of glutaryl-7 aminoadipyl cephalosporanic acid (glutaryl-7ADCA) to 7-aminoadipylcephalosporanic acid(7-ADCA). The cells expressing the glutaryl cephalosporin amidase were harvested by centrifugation. The cell pellets were resuspended in water and the cells were disrupted by sonication. Cellular debris were removed by centrifugation and the clarified supernatant obtained was used for assays. The clarified supernatant diluted to the appropriate concentration at a volume of 250 μl was added to an equal volume of pre-warmed 20 mg/ml glutaryl-7-ADCA in 0.3M Tris buffer, pH8.0. The reaction mixtures were incubated in a gyratory incubator at 37° C. at 330 rpm for 30 minutes. The reaction was stopped by the addition of 4 ml of 25 mM $H_2SO_4$. The reaction mixtures were clarified by centrifugation and the 5 μl of the sample was injected onto a 5 micron Phenosphere C18 column and the products eluted with 95% 60 mM ammonium acetate and 5% acetonitrile.

Assay of Penicillin G Amidase Activity

The cells expressing the penicillin G amidase were harvested by centrifugation and the cell pellets were resuspended in water. The cells were disrupted by sonication and the cell lysates assayed for penicillin G amidase activity. One ml of the appropriately dilute supernatant was added to one ml of prewarmed 4.5% potassium penicillin G prepared in 200 mM potassium phosphate buffer, pH7.5. The reaction mixtures were incubated in a gyratory incubator at 37° C. for 15 minutes. The reactions were stopped by the addition of one ml of 99.0% $CH_3CN$ and 1.0% HOAC, mixed, and clarified by centrifugation. One ml of the reaction mixture was mixed with 0.33 ml of p-dimethyl aminobenzaldehyde (PDAB) reagent: one part 1% PDAB in methanol plus 6 part sodium acetate buffer (1000 ml glacial acetic acid, 475 ml deionized water, and 25 ml 1 N sodium hydroxide). Following incubation for 4 minutes at room temperature, the absorbance at 415 nm is measured, from which the molar conversion is calculated.

Construction of pBMS1000

Plasmid pBM11M5 was digested with Pvu I and Cla I. The 3'-overhang and 5' overhang bases were removed by treatment with T4 polymerase and Klenow fragment, respectively. The 4.4Kb fragment was electroeluted and ligated. The resultant plasmid, named pBM11M5(Cla/Pvu), was subjected to partial Hind III digestion. The linearized fragment was electroeluted, the 5'-overhang filled in with Klenow fragment, and ligated. Restriction analyses were performed to select for the plasmid with the HindIII site eliminated at the correct position. The resultant plasmid, named pBM11M5(Cla/Pvu/H3) was digested with Hind III and BamH I. The 3.35 Kb fragment was eluted and ligated to the 90 bp tac promoter obtained by the digestion of plasmid pDR540 with Hind III and BamH I. The resultant plasmid, named pBM11tac, was digested with EcoR I and Hind III, yielding a 2.9 Kb fragment which was ligated to the 1.3 Kb lac$^{iQ}$ fragment obtained by the digestion of pUC19lac$^{iQ}$ with EcoRI and HindIII. To facilitate the cloning of heterologous genes, an Nco I cloning site was introduced immediately after the BamH I of the tac promoter by inserting the adapter 5'-GATCTCCATGGG-3' (SEQ.ID.NO.:5)

3'-AGGTACCCCTAG-5' (SEQ.ID.NO.:6) to the BamHI site of plasmid pBM11taclac. The resultant 4.2 Kb plasmid was named pBMS1000.

Construction of pBMS1000GroESL

Plasmid pBMS1000 was digested with restriction enzymes, NcoI and SmaI. The resultant 4.2 Kb fragment was ligated to the groELS gene obtained via PCR amplifications and digested with NcoI and SmaI as described above. The resultant 6.2 Kb plasmid was named pBMS1000GroESL.

Construction of pBMS1999GCA

Plasmid pBM11 taclacλN203GCA is a fusion expression plasmid derived from pBMS1000 containing DNA coding for the first 33 amino acids of the phage λN protein fused to the amino terminus of the 203 glutaryl ceph amidase gene (203GCA). The λ N protein fusion portion may be removed by digestion with NcoI (5' end) and BspH1 (3' end). Plasmid pBM11taclacλN203GCA was digested with BspHI and the 5' overhang filled with Klenow fragment followed by digestion with NcoI. The 6.1 kb fragment was electroeluted and ligated to the 403 base pair fragment containing the complete gene sequence for the groES gene and the first 7 amino acids of the groEL gene. Thus, the GCA protein is a fusion product of the groEL gene. This fragment was generated by the digestion of plasmid pBM11taclacGroESL with restriction enzymes, Nco I and Rsa I followed by electroelution. The resultant 6.5 Kb plasmid was named pBMS1999GCA.

Construction of pBMS2000GCA and pET9dGCA

Plasmid pBMS1999 was digested with Mfe I and BspH I. The 6.43 kb fragment was purified from the gel by electroelution and ligated to the following synthetic adapter:

```
                            groES
Mfe I                       stop
5'-A ATT GTT GAA GCG TAA
   TCCGCGCACGACACTGAACATACGAATTTAAGGAAT(SEQ.ID.NO.:7)

3'-     CAA CTT CGC ATT
   AGGCGCGTGCTGTGACTTGTATGCTTAAATTCCTTA(SEQ.ID.NO.:8)

BspHI
   AAAGAT-3'(SEQ.ID.NO.:9)

TTTCTA GTAC-5'(seq.ID.NO.:10)
```

The resultant plasmid was named pBMS2000GCA. This plasmid has the intact groES gene, the intergene region between groES and groEL gene followed by the sequence coding for the 203 glutaryl ceph amidase gene.

Plasmid pET9d (purchased from Novogen) was digested with restriction enzyme, NcoI and BamHI. The linearized 4.3 Kb plasmid DNA was purified from the agarose gel by electroelution and ligated to the 2 Kb glutaryl cephalosporin amidase gene obtained by digestion of a plasmid containing the GCA203 gene with BspH I and BamH I. The resultant plasmid was named pET9dGCA.

Construction of pBMS2000

Plasmid pBMS2000 was derviyed from plasmid pBMS2000GCA. Plasmid pBMS20GCA was digested with restriction enzymes, MfeI and BamHI to remove the GCA gene. The resultant 4.53 Kb fragment was ligated to the following the oligomer The resultant 4.6 Kb plasmid was named pBMS2002. This plasmid contains the intact groES gene, the intergene region between groES and groEL followed by restriction sites Ndel and BamHI for gene cloning.

Construction of pBMS2000.103

Plasmid pBMS2000.103 is derived from plasmid pBMS2000. It lacks the sequence coding for the groES gene but retains the intergenic sequences between the groES/

```
                    MfeI                      BspHI BamHI
5'AATTGTTGAAGCGTAATCCGCGCACGACACTGAACATAATTT            (SEQ.ID.NO.:11)
 AAGGAATAAAGATCATCACCCG

3'
 CAACTTCGCATTAGGCGCGTGCTGTGACTTGTATTAAATTCCTTATTTCTA (SEQ.ID.NO.:12)
 CTAGTGGGCTAG
```

The resultant plasmid was named pBMS2000. This plasmid contains the intact groES gene, the intergene region between groES and groEL, and BspHI and BamHI restriction sites for gene cloning.

Construction of pBMS2001

Plasmid pBMS2001 was derived from plasmid pBMS2000. Plasmid pBMS2000 was digested with restriction enzymes, MfeI and BamHI. The resultant 4.53 Kb fragment was ligated to the following oligomer groEL genes. Plasmid pBMS2000 was digested with restriction enzymes, HindIII and BspHI. This process removes the tac promoter, the lac operator, the groES gene and the groES/groEL intergenic region. The resultant 4.12 Kb fragment was ligated to a chemically synthesized oligomer which contains the sequences of the tac promoter, the lac operator, and the groES/groEL intergenic region. HindIII

```
                              MfeI
NcoI  BamHI
5'AATTGTTGAAGCGTAATCCGCGCACGACACTGAACATAATTTAAGGAAT (SEQ.ID.NO.:13)
 AAAGACCATGGCCCG

3'
 CAACTTCGCATTAGGCGCGTGCTGTGACTTGTATTAAATTCCTTATTTCT  (SEQ.ID.NO.:14)
 GGTACCGGGCTAG
```

The resultant plasmid was named pBMS2001. This plasmid contains the intact groES gene, the intergene region between groES and GroEL followed by restriction sites NcoI and BamHI for gene cloning.

Construction of pBMS2002

Plasmid pBMS2002 was derived from plasmid pBMS2000. Plasmid pBMS2000 was digested with restriction enzymes, MfeI and BamHI. The resultant 4.53 Kb fragment was ligated to the following oligomer

```
                              MfeI
NdeI  BamHI
5'AATTGTTGAAGCGTAATCCGCGCACGACACTGAACATAATTTAAGGAAT (SEQ.ID.NO.:15)
 AAACATATGCCCG

3'
 CAACTTCGCATTAGGCGCGTGCTGTGACTTGTATTAAATTCCTTATTTGT  (SEQ.ID.NO.:16)
 ATACGGCTAG
```

```
              HindIII
              AGCTTGTTGACAATTAATCAACGGCTCGTATAATGTGTGGAATTGTGAGC (SEQ.ID.NO.:17)
              GGATAACAATTTCCGCGCAC

ACAACTGTTAATTAGTTGCCGAGCATATTACACACCTTAACACTCGCCTA (SEQ.ID.NO.:18)
```

```
                        -continued
TTCTTAAAGGCGCGAG

BspHI
GACACTGAACATACGAATTTAAGGAATAAAGAT                  (SEQ.ID.NO.:19)
CTGTGACTTGTATGCTTAAATTCCTTATTTCTAGTAC
The resultant 4.2 Kb plasmid is named pBMS2000.103.
```

Construction of pBMS2000.75

Plasmid pBMS2000.75 similar to plasmid pBMS2000.103. It contains only partial groES/groEL intergenic sequences rather than the complete intergenic sequences as in plasmid pBMS2000.103. Plasmid pBMS2000 was digested with restriction enzymes, HindIII and BspHI. This process removes the tac promoter, the groES gene and the groES/groEL intergenic region. The resultant 4.1 Kb fragment was ligated to a chemically synthesized oligomer which contains the sequences of the tac promoter, the lac operator, and the partial groES/groEL intergenic region.

```
HindIII
AGCTTGTTGACAATTAATCAACGGCTCGTATAATGTGTGGAATTGTGAGC  (SEQ,ID.NO.:20)
GGATAACAATTTAAGGAAGA ACAACTGTTAATTAGTTGCCGAGCATATTACACACCTTAACACTCGCCTA  (SEQ.ID.NO.:21)
TTCTTAAATTCCTTAT BspHI
AAGAT                                              (SEQ.ID.NO.:22)
TTCTAGTAC
The resultant 4.2 Kb plasmid is named pBMS2000.75.
```

Construction of pBMS2000H

Plasmid pBMS1000 was digested with restriction enzymes, HindIII and NcoI. The 4.1 Kb fragment was isolated, electroeluted and ligated to the following oligomer

```
HindIII
5'AGCTTACTCCCCATCCCCCTGTTGACAATTAATCATCGGCTCGTATAAT (SEQ.ID.NO.:23)
GTGTGGTCCGCGCACGACA 3'-
ATGAGGGGTAGGGGGACAACTGTTAATTAGTAGCCGAGCATATTACACA  (SEQ.ID.NO.:24)
CCAGGCGCGTGCTGT                    NcoI

CTGAACATACGAATTTAAGGAATAAAAAGAC-3'                  (SEQ.ID.NO.:25)

GACTTGTATGCTTAAATTCCTTATTTTTCTGGTAC-5'              (SEQ.ID.NO.:26)
```

The resultant 4.2 Kb plasmid named pBMS2000H contains the tac promoter followed by intergenic space sequences between the groES and groEL gene. It does not contain the operator sequences thus rendering any heterologous gene cloned in this vector to be expressed constitutively.

Construction of pBMS1000PGA, pET9d and pBMS2000PGA

The resultant PCR product from the amplification of PGA gene was digested with restriction enzymes, BspH I and BamH I and cloned between the NcoI and BamH I sites of pBMS1000, the NcoI and BamH I sites of pET9d (purchased from Novogen) and the BspH I and BamH I sites of pBMS2000 resulting in pBMS1000PGA, pET9dPGA and pBMS2000PGA respectively.

Construction of pBMS2000HGCA

Plasmid pBMS2000H was digested with restriction enzymes, NcoI and BamHI. The 4.2 Kb was isolated by electroelution and ligated to the 2Kb glutaryl cephalosporin amidase gene obtained by digestion of a plasmid containing the GCA203 gene with BspHI and BamHI. The resultant 6.2 Kb plasmid was named pBMS2000GCA.

Construction of pBMS2000.103GCA and pBMS2000.75GCA

Plasmids pBMS2000.103 and PBMS2000.75 were digested with restriction enzymes, BspHI and BamHI. The 4.2 Kb fragment was electroeluted and ligated to the 2Kb glutaryl cephalosporin amidase gene obtained by digestion of a plasmid containing the GCA203 gene with BspHI and BamHI. The resultant 6.2 Kb plasmid was named pBMS2000.103GCA and pBMS2000.75GCA.

TABLE II

Expression of glutaryl cephalosporin amidase 203 in various plasmids

| Plasmid | IU/ml |
|---|---|
| pBMS1000INGCA203 | 1.7 |
| pET9GCA203 | 6.7 |
| pBMS2000GCA203 | 8.4 |

Overnight cultures of E. coli harboring the GCA203 were diluted 1:10 in T-broth supplemented with 30 µg/ml of neomycin sulfate. The cultures were grown at 30° C. at 300 rpm for 4 hours or until $OD_{550}$=2.0. At that time point, 60 µM of IPTG was added to the cultures to induce the expression of GCA.

TABLE III

Expression of glutaryl cephalosporin amidase 203 in various plasmids in fermentation tanks

| Plasmid IU/ml | Vessel size | |
|---|---|---|
| | 2-l | 4000-l |
| pBMS1000GCA | 54 | 20 |
| pET9GCAGCA | 120 | 50 |
| pBMS2000GCA | 280 | 150 |

TABLE IV

Expression of fusion and native GCA in shake flasks and 1-liter fermentors

| Plasmid | Shake flask titer iu/ml | 1-liter titer iu/ml |
|---|---|---|
| pBMS1999GCA | 5.2 | 100 |
| pBMS2000GCA | 8.4 | 220 |

TABLE V

Comparison of penicillin G amidase expression in pBMS2000 to pET vector

| Plasmid | IU/ml |
|---|---|
| pET9PGA | 1.0 |
| pBMS2000PGA | 3.3 |

Overnight cultures of *E. coli* harboring the penicillin G amidase were diluted 1:10 in T-broth supplemented with 30 μg/ml of neomycin sulfate. The cultures were grown at 30° C. at 300 rpm for 4 hours or until $OD_{550}$=2.0. At that time point, 60 μM of IPTG was added to the cultures to induce the expression of penicillin G amidase.

TABLE VI

Expression of glutaryl cephalosporin amidase 203 in various derivatives of plasmid pBMS2000

| Plasmid | iu/ml |
|---|---|
| pBMS2000GCA | 11 |
| pBMS2000 · 103GCA | 9 |
| pBMS2000HGCA | 11 |

Overnight cultures of *E. coli* harboring the GCA203 were diluted 1:10 in T-broth supplemented with 30 μg/ml of neomycin sulfate. The cultures were grown at 30° C. at 300 rpm for 4 hours or until $OD_{550}$=2.0. At that time point, 6 μM of IPTG was added to the cultures to induce the expression of GCA.

What is claimed is:

1. An expression vector comprising:
   (a) tac promoter,
   (b) groESL integenic region of DNA,
   (c) the start codon of the groEL gene sequence,
   (d) a restriction site and,
   (e) a heterologous gene sequence;
   provided that said expression vector contains no more than the first seven codons of the groEL gene.

2. The expression vector of claim 1 further comprising groES DNA.

3. The expression vector of claim 1 further comprising the first seven codons of groEL and wherein the RsaI site is modified to contain a restriction site different from the RsaI restriction site.

4. The expression vector of claim 1 wherein the restriction site is introduced immediately before the start codon of the groEL gene.

5. The expression vector of claim 1 further comprising an origin of replication and a DNA sequence which encodes a selectable marker.

6. The expression vector of claim 5 wherein the selectable marker is antibiotic resistance.

7. The expression vector of claim 5 wherein the selectable marker is neomycin resistance.

8. The expression vector of claim 1 further comprising sequences coding for the lac repressor.

9. The expression vector of claim 1 having all of the identifying characteristics of plasmids pBMS1999, pBMS2000, or pBMS2001.

10. A prokaryotic host cell containing an expression vector comprising:
    (a) tac promoter,
    (b) groESL integenic region of DNA,
    (c) the start codon of the groEL gene sequence,
    (d) a restriction site and,
    (e) a heterologous gene sequence;
    provided that said expression vector contains no more than the first seven codons of the groEL gene.

11. The prokaryotic host cell of claim 10 wherein said expression vector further comprises groES DNA.

12. The prokaryotic host cell of claim 10 which is E. coli.

13. The E. coli host cell of claim 12 wherein the expression vector further comprises an origin of replication and a DNA sequence which encodes a selectable marker.

14. The E. coli host cell of claim 12 wherein the selectable marker is neomycin phosphotransferase.

15. The E. coli host cell of claim 10 wherein the expression vector has all of the identifying characteristics of plasmids pBMS1999, pBMS2000, or pBMS2001.

16. An E. coli strain having the designation ATCC 98563.

17. A method for expressing a heterologous protein is a prokaryotic host cell comprising culturing a prolkaryotic host cell containing an expression vector comprising:
    (a) tac promoter,
    (b) groESL integenic region of DNA,
    (c) the start codon of the groEL gene sequence,
    (d) a restriction site and,
    (e) a heterologous gene sequence;
    provided that said expression vector contains no more than the first seven codons of the groEL gene.

18. The method of claim 17 wherein said expression vector further comprises groES DNA.

19. The method of claim 17 wherein the prokaryotic host cell is E. coli.

20. The method of claim 17 wherein the expression vector further comprises an origin of replication and a DNA sequence which encodes a selectable marker.

21. The method of claim 20 wherein the selectable marker is antibiotic resistance to neomycin sulfate.

22. The method of claim 17 wherein the heterologous protein is glutaryl cephalosporin amidase or penicillin G amidase.

23. The method of claim 17 wherein the expression vector further comprises sequences coding for the lac repressor.

24. The method of claim 17 carried out at a temperature of about 25° C. to about 37° C. and a pH of about 7.0 to about 7.2.

* * * * *